(12) United States Patent
Abdolahad et al.

(10) Patent No.: US 10,914,708 B2
(45) Date of Patent: Feb. 9, 2021

(54) IN-SITU MICROBUBBLES GENERATION FOR ULTRASONIC BIOMEDICAL APPLICATIONS

(71) Applicants: Mohammad Abdolahad, Tehran (IR); Mohammad Ali Khayamian, Tehran (IR); Ashkan Zandi, Tehran (IR)

(72) Inventors: Mohammad Abdolahad, Tehran (IR); Mohammad Ali Khayamian, Tehran (IR); Ashkan Zandi, Tehran (IR)

( * ) Notice: Subject to any disclaimer, the term of this patent is extended or adjusted under 35 U.S.C. 154(b) by 358 days.

(21) Appl. No.: 15/960,524

(22) Filed: Apr. 23, 2018

(65) Prior Publication Data

US 2018/0251901 A1    Sep. 6, 2018

Related U.S. Application Data

(60) Provisional application No. 62/488,873, filed on Apr. 24, 2017, provisional application No. 62/488,875, filed on Apr. 24, 2017.

(51) Int. Cl.
*G01N 27/48* (2006.01)
*G01N 27/327* (2006.01)
(Continued)

(52) U.S. Cl.
CPC ............ *G01N 27/48* (2013.01); *A61B 5/1473* (2013.01); *C23C 14/0005* (2013.01); *C23C 14/022* (2013.01); *C23C 14/205* (2013.01); *C23C 14/3464* (2013.01); *C23C 14/5806* (2013.01); *C23C 14/5846* (2013.01); *C25B 1/02* (2013.01); *C25B 9/06* (2013.01); *C25B 11/0405* (2013.01); *C25B 11/0415* (2013.01); *C25B 11/0478* (2013.01); *G01N 27/327* (2013.01);
(Continued)

(58) Field of Classification Search
CPC ........................................................ C25B 1/02
See application file for complete search history.

(56) References Cited

U.S. PATENT DOCUMENTS 9,364,569 B2    6/2016  Schneider et al.
2005/0067304 A1*  3/2005  King ..................... C25D 21/12
                                                                          205/794

OTHER PUBLICATIONS

Z. Fan et al., "Intracellular Delivery and Calcium Transients Generated in Sonoporation Facilitated by Microbubbles", J Control Release, Feb. 25, 2010 142(1), pp. 31-51.

(Continued)

*Primary Examiner* — Brian W Cohen
(74) *Attorney, Agent, or Firm* — Bajwa IP Law Firm; Haris Zaheer Bajwa

(57) ABSTRACT

A method for in-situ generation of microbubbles is disclosed. The method includes preparing an electrochemical apparatus, where the electrochemical apparatus includes a substrate and an integrated three-electrodes array patterned on the substrate. The integrated three-electrodes array includes a working electrode, a reference electrode, and a counter electrode. The method further includes growing a nano-structured layer on the working electrode of the integrated three-electrodes array, putting the electrochemical apparatus in contact with a medium fluid, electrolyzing the medium fluid by applying an instantaneous electrical potential to the electrochemical apparatus, and generating a plurality of microbubbles around the electrochemical apparatus in contact with the medium fluid responsive to electrolyzing of the medium fluid.

19 Claims, 23 Drawing Sheets

(51) Int. Cl.

| | |
|---|---|
| *C23C 14/02* | (2006.01) |
| *G01N 33/483* | (2006.01) |
| *C23C 14/58* | (2006.01) |
| *C23C 14/34* | (2006.01) |
| *G03F 7/20* | (2006.01) |
| *C23C 14/20* | (2006.01) |
| *A61B 5/1473* | (2006.01) |
| *C23C 14/00* | (2006.01) |
| *C25B 1/02* | (2006.01) |
| *C25B 9/06* | (2006.01) |
| *C25B 11/04* | (2006.01) |
| *G01N 33/49* | (2006.01) |

(52) U.S. Cl.
CPC ......... *G01N 33/4833* (2013.01); *G01N 33/49* (2013.01); *G03F 7/70* (2013.01)

(56) References Cited

OTHER PUBLICATIONS

Truong An Tran et al., "Characterization of Cell Membrane Response to Ultrasound Activated Microbubbles", IEEE transactions on ultrasonics, ferroelectrics, and frequency control, Jan. 2008, vol. 55, No. 1, pp. 44-49.

Spiros Kotopoulis et al., "Treatment of human pancreatic cancer using combined ultrasound, microbubbles, and gemcitabine: A clinical case study", Med. Phys. Jul. 2013, 40 (7), pp. 072902-1 to 072902-9.

\* cited by examiner

708

710

IN-SITU MICROBUBBLES GENERATION FOR ULTRASONIC BIOMEDICAL APPLICATIONS

CROSS-REFERENCE TO RELATED APPLICATION

This application claims the benefit of priority from U.S. Provisional Patent Application Ser. No. 62/488,873 filed on Apr. 24, 2017, and entitled "ELECTROCHEMICAL APPROACH FOR SENSING SONOPORATION OF A CELL" and U.S. Provisional Patent Application Ser. No. 62/488,875 filed on Apr. 24, 2017, and entitled "ULTRASOUND-ASSISTED ELECTROCHEMICAL DISTINCTION OF NORMAL AND CANCEROUS CELLS", which are both incorporated herein by reference in their entirety.

SPONSORSHIP STATEMENT

This application has been sponsored by Iran Patent Office, which does not have any rights in this application.

TECHNICAL FIELD

The present disclosure generally relates to in-situ generation of microbubbles for ultrasonic biomedical applications, and particularly, to an apparatus and method for in-situ generating microbubbles in a patient body fluid for ultrasonic-conducting medical applications.

BACKGROUND

Commercial microbubbles are used as Ultrasound Contrast Agents (UCA) in biomedical ultrasonic applications, such as ultrasonic imaging (e.g., Sonography and Echocardiography) and sonoporation of cells (e.g., for drug delivery and gene therapy). Using microbubbles aids in enhancing efficiency of ultrasonic-assisted biomedical applications due to induction of cavitation phenomenon into the tissue by such microbubbles. For instance, using commercial microbubbles may increase the contrast of sonography images.

Commercial microbubbles generally include a core and shell structure, where the core includes a gas agent coated with a polymeric shell. Using these commercial microbubbles involves inserting an external element or media into a patient body that may cause some biological incompatibilities due to the presence of the gas agent coated with the polymeric shell. Also, producing and using commercial microbubbles requires complicated and costly methods and devices.

Hence, there is a need for a simple, cost-effective, fast, and capable of in-situ conducting method for generation of microbubbles which does not require the use of commercial microbubbles, which would be external elements that would enter the body or any bio-system. Also, there is a need for in-situ production of microbubbles in a patient's body fluid at any location, where a medical operation needs to be conducted or a delivery process needs to be facilitated. Furthermore, there is a need for an apparatus for in-situ microbubbles generation that does not require insertion of an external material into a biological sample for both in-vitro and in-vivo applications.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for in-situ generation of microbubbles. The method may include preparing an electrochemical apparatus, where the electrochemical apparatus may include a substrate, and an integrated three-electrodes array patterned on the substrate. The integrated three-electrodes array may include a working electrode, a reference electrode, and a counter electrode. The method may further include growing a nano-structured layer on the working electrode of the integrated three-electrodes array, putting the electrochemical apparatus in contact with a medium fluid, electrolyzing the medium fluid by applying an instantaneous electrical potential to the electrochemical apparatus, and generating a plurality of microbubbles around the electrochemical apparatus in contact with the medium fluid responsive to the electrolyzing the medium fluid.

In an exemplary implementation, the substrate may include one of a glass slide, Poly(methyl methacrylate) (PMMA), a silicon wafer, and combinations thereof. The integrated three-electrodes array may include one of a circular-patterned array, an interdigital-patterned array, a needle-shaped array, and combinations thereof.

In an exemplary implementation, preparing the electrochemical apparatus may include depositing an electrical conductive layer on a surface of the substrate by Radio Frequency (RF) sputtering, and forming a pattern of the integrated three-electrodes array on the electrical conductive layer using photolithography technique. In an exemplary embodiment, the electrical conductive layer may include one of a mechanically-resistant material in reactive ion etching (RIE) system, a thick metal layer, a Gold/Titanium (Au/Ti) bilayer, a layer of Chrome (Cr), a layer of Gold (Au), and combinations thereof.

In an exemplary implementation, preparing the electrochemical apparatus may include depositing a Gold/Titanium (Au/Ti) bilayer on the substrate, and patterning the integrated three-electrodes array on the Au/Ti bilayer using photolithography technique. Depositing the Gold/Titanium (Au/Ti) bilayer on the substrate may include depositing a Ti layer on the substrate using a Radio Frequency (RF) sputtering system, and depositing an Au layer on the Ti layer using the Radio Frequency (RF) sputtering system.

In an exemplary implementation, preparing the electrochemical apparatus may further include treating the substrate by forming a non-conductive substrate from the substrate before depositing the electrical conductive layer on the surface of the substrate by Radio Frequency (RF) sputtering. In another exemplary implementation, preparing the electrochemical apparatus may further include separating the integrated three-electrodes array from the substrate by vertical etching of the pattern of the integrated three-electrodes array using a reactive ion etching (RIE) system.

In an exemplary implementation, growing the nano-structured layer on the working electrode of the integrated three-electrodes array may include seeding a seeding solution on a surface of the working electrode, growing the nano-structured layer on the surface of the working electrode, and post-processing the nano-structured layer grown on the working electrode. In an exemplary embodiment, the nano-structured layer may include a layer of one of carbon nanotubes (CNTs), ZnO, Silicon nanowires (SiNWs), Silicon nanograss, $TiO_2$ nanotubes, $TiO_2$ nanowires, and combinations thereof.

In an exemplary implementation, seeding the seeding solution on the surface of the working electrode may include wetting the surface of the working electrode by the seeding solution, spin-coating the seeding solution on the surface of the working electrode, and annealing the electrochemical apparatus at a temperature of more than about 250° C. for a time duration between about 10 seconds and about 30 seconds. In an exemplary embodiment, growing the nano-structured layer on the surface of the working electrode may include placing the electrochemical apparatus in a sealed container containing a growth solution, and heating the sealed container uniformly at a temperature between about 70° C. and about 100° C. In an exemplary embodiment, post-processing the nano-structured layer grown on the working electrode may include annealing the electrochemical apparatus at a temperature of more than about 250° C. for about 30 minutes.

In an exemplary implementation, putting the electrochemical apparatus in contact with the medium fluid may include one of inserting the integrated three-electrodes array into a human body, inserting the integrated three-electrodes array into a cancer tumor, putting the electrochemical apparatus inside a biological solution, inserting the electrochemical apparatus into a cell culture medium, and combinations thereof. In an exemplary embodiment, the medium fluid may include a body fluid, for example, a blood sample.

In an exemplary implementation, electrolyzing the medium fluid by applying the instantaneous electrical potential to the electrochemical apparatus may include connecting the electrochemical apparatus to an electrochemical stimulator-analyzer system, and applying the instantaneous electrical potential to the working electrode using the stimulator-analyzer system. In an exemplary embodiment, the electrochemical stimulator-analyzer system may include a potentiostat.

In an exemplary embodiment, electrolyzing the medium fluid by applying the instantaneous electrical potential to the electrochemical apparatus may include applying a DC signal with a voltage between about −3 V and about −0.5 V for a time duration less than about 1 seconds to the electrochemical apparatus using the stimulator-analyzer system. In an exemplary embodiment, electrolyzing the medium fluid by applying the instantaneous electrical potential to the electrochemical apparatus may include electrolyzing the medium fluid using a cyclic voltammetry (CV) technique.

In an exemplary implementation, generating the plurality of microbubbles around the electrochemical apparatus in the medium fluid responsive to the electrolyzing the medium fluid may include generating a plurality of microbubbles around the working electrode. In an exemplary embodiment, the plurality of microbubbles may include a plurality of $H_2$ microbubbles generated by electrolyzing the medium fluid.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
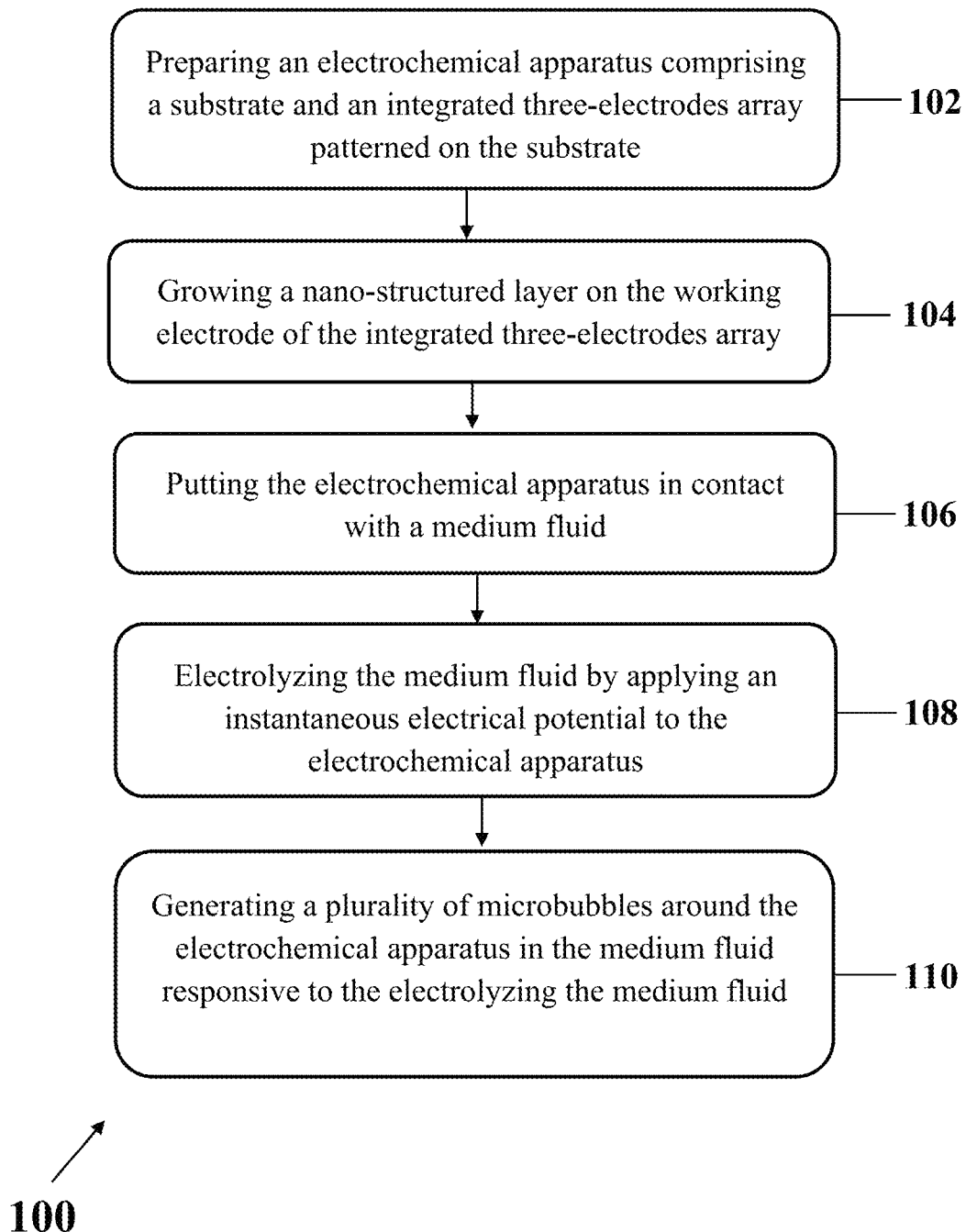
FIG. 1A illustrates an exemplary implementation of a method for in-situ generation of microbubbles, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein, a method and apparatus for in-situ generation of microbubbles from a cell culture media, a patient's blood, or a patient's body fluid is disclosed. Such microbubbles may be generated in-situ before or during ultrasonic biomedical applications, such as ultrasonic imaging (e.g., Sonography and Echocardiography), and sonoporation of cells (e.g., for drug delivery, gene therapy, and cancer diagnosis). So, there is no need to insert externally commercial microbubbles into the patient's body to enhance an ultrasonic biomedical procedure.

Exemplary method may include an electrochemical stimulation of a medium fluid using an electrochemical apparatus, which may include a cell culture media, a patient's blood, or generally a patient's body fluid. Exemplary electrochemical apparatus may include an integrated three-electrodes array on a chip or three needles fixed adjacently by a holding member. Exemplary electrochemical apparatus may be connected to a potentiostat device and may be placed within an exemplary medium fluid, for example, an exemplary electrochemical apparatus may be inserted into a tumor site of a patient's body. Then, an instantaneous voltage may be applied to the electrochemical apparatus via the potentiostat; thereby, resulting to generation of microbubbles. The generated microbubbles may be used in ultrasonic-electrochemical diagnosis of cancer, ultrasonic imaging of a patient body, or any other ultrasonic-assisted biomedical applications. In some implementations, exemplary electrochemical apparatus may include a circular-patterned array or an interdigital-patterned array (a comb-patterned array) for use in in-vitro biomedical applications. In some implementations, exemplary electrochemical apparatus may include a needle-shaped array for use in both in-vitro and in-vivo biomedical applications.

FIG. 1A shows an exemplary implementation of method 100 for in-situ generation of microbubbles, consistent with one or more exemplary embodiments of the present disclosure. Exemplary method 100 may include preparing an electrochemical apparatus (step 102), where the electrochemical apparatus may include a substrate and an integrated three-electrodes array patterned on the substrate. The integrated three-electrodes array may include a working electrode, a reference electrode, and a counter electrode. Method 100 may further include growing a nano-structured layer on the working electrode of the integrated three-electrodes array (step 104), putting the electrochemical apparatus in contact with a medium fluid (step 106), electrolyzing the medium fluid by applying an instantaneous electrical potential to the electrochemical apparatus (step 108), and generating a plurality of microbubbles around the electrochemical apparatus in the medium fluid responsive to the electrolyzing of the medium fluid (step 110).

Figure 1B:
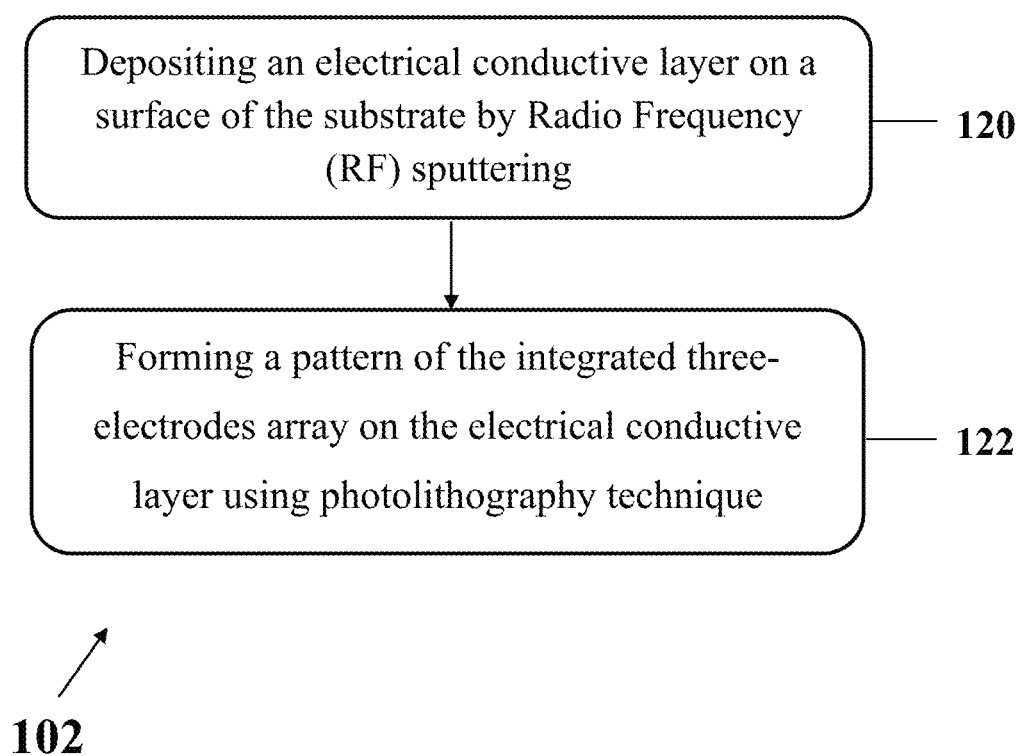
FIG. 1B illustrates an exemplary implementation of a process for preparing the electrochemical apparatus, consistent with one or more exemplary embodiments of the present disclosure.

Step 102 may include preparing the electrochemical apparatus. FIG. 1B shows an exemplary implementation of a process for preparing the electrochemical apparatus (step 102), consistent with one or more exemplary embodiments of the present disclosure. Preparing an exemplary electrochemical apparatus may include depositing an electrical conductive layer on a surface of the substrate by Radio Frequency (RF) sputtering (step 120), and forming a pattern of the integrated three-electrodes array on the electrical conductive layer using photolithography technique (step 122). In an exemplary embodiment, the substrate may include one of a glass slide, Poly(methyl methacrylate) (PMMA), a silicon wafer, and combinations thereof. In an exemplary embodiment, the electrical conductive layer may include one of a mechanically-resistant material in a reactive ion etching (RIE) system, a Gold/Titanium (Au/Ti) bilayer, and combinations thereof. In an exemplary embodiment, the mechanically-resistant material in the reactive ion etching (RIE) system may include a thick metal layer. In an exemplary embodiment, the mechanically-resistant material in the reactive ion etching (RIE) system may include a layer of Chrome (Cr) or Gold (Au).

In an exemplary implementation, preparing the electrochemical apparatus (step 102) may include depositing a Gold/Titanium (Au/Ti) bilayer on the substrate (step 120), and patterning the integrated three-electrodes array on the Au/Ti bilayer using photolithography technique (step 122). Depositing the Gold/Titanium (Au/Ti) bilayer on the substrate may include depositing a Ti layer on the substrate using a Radio Frequency (RF) sputtering system and depositing an Au layer on the Ti layer using the Radio Frequency (RF) sputtering system.

Figure 1C:
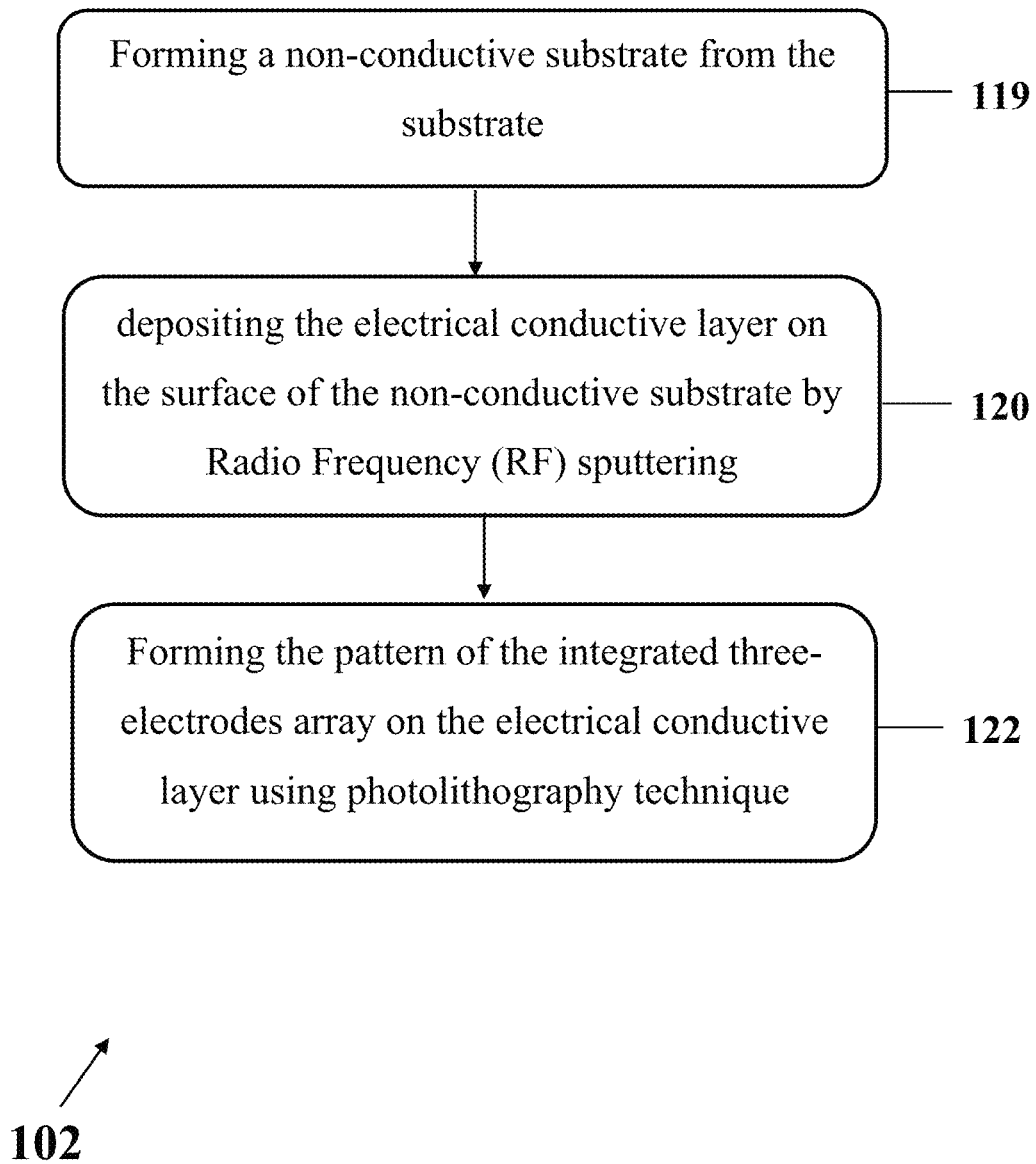
FIG. 1C illustrates an exemplary implementation of a process for preparing the electrochemical apparatus, consistent with one or more exemplary embodiments of the present disclosure.

In an exemplary implementation, preparing the electrochemical apparatus may further include treating the substrate by forming a non-conductive substrate from the substrate before depositing the electrical conductive layer on the surface of the substrate by Radio Frequency (RF) sputtering. FIG. 1C shows an exemplary implementation of a process for preparing the electrochemical apparatus (step 102), consistent with one or more exemplary embodiments of the present disclosure. Preparing an exemplary electrochemical apparatus may include forming the non-conductive substrate from the substrate (step 119), depositing the electrical conductive layer on the surface of the non-conductive substrate by Radio Frequency (RF) sputtering (step 120), and forming the pattern of the integrated three-electrodes array on the electrical conductive layer using photolithography technique (step 122). In an exemplary embodiment, the non-conductive substrate may include an electrically non-conductive substrate. In an exemplary embodiment, the non-conductive substrate may include the substrate with a layer of non-electrically conductive layer coated on the substrate.

In an exemplary embodiment, forming the non-conductive substrate from the substrate may include heating the substrate in a furnace at a temperature of more than 1000° C. for about 1 hour or more. In an exemplary embodiment, forming the non-conductive substrate from the substrate may include annealing the substrate in order to make the substrate electrically non-conductive.

Figure 2A:
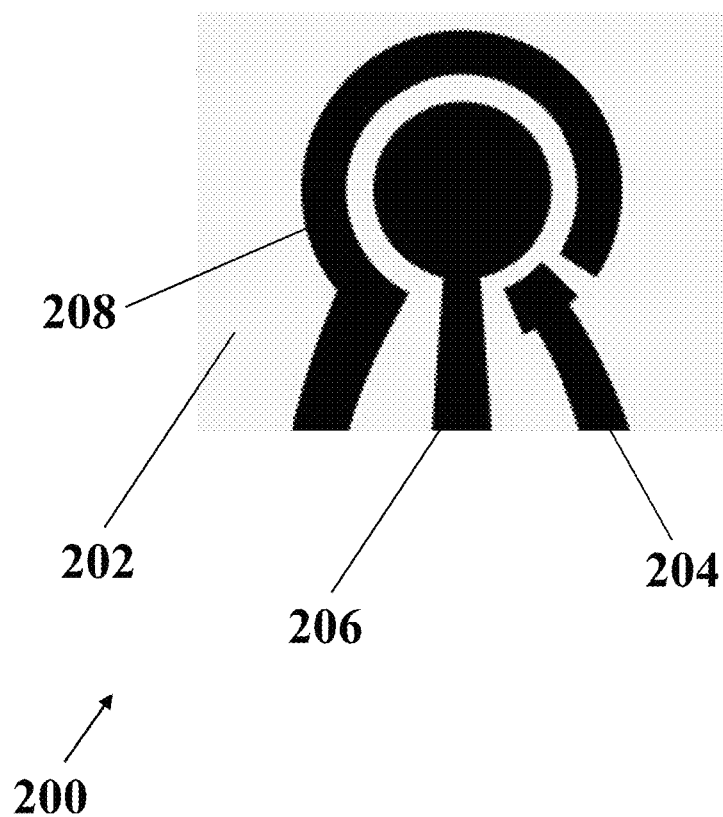
FIG. 2A illustrates a schematic top view of an exemplary electrochemical apparatus with a circular-patterned array of electrodes, consistent with one or more exemplary embodiments of the present disclosure.

In an exemplary implementation, exemplary integrated three-electrodes array of exemplary electrochemical apparatus may include a circular-patterned array of electrodes or an interdigital-patterned array of electrodes that may include a comb-patterned array of electrodes. FIG. 2A shows a schematic top view of an exemplary electrochemical apparatus 200 with a circular-patterned array of electrodes, consistent with one or more exemplary embodiments of the present disclosure. Exemplary circular-patterned array of electrodes may include reference electrode 204, working electrode 206, and counter electrode 208, which may be patterned on exemplary substrate 202.

Figure 2B:
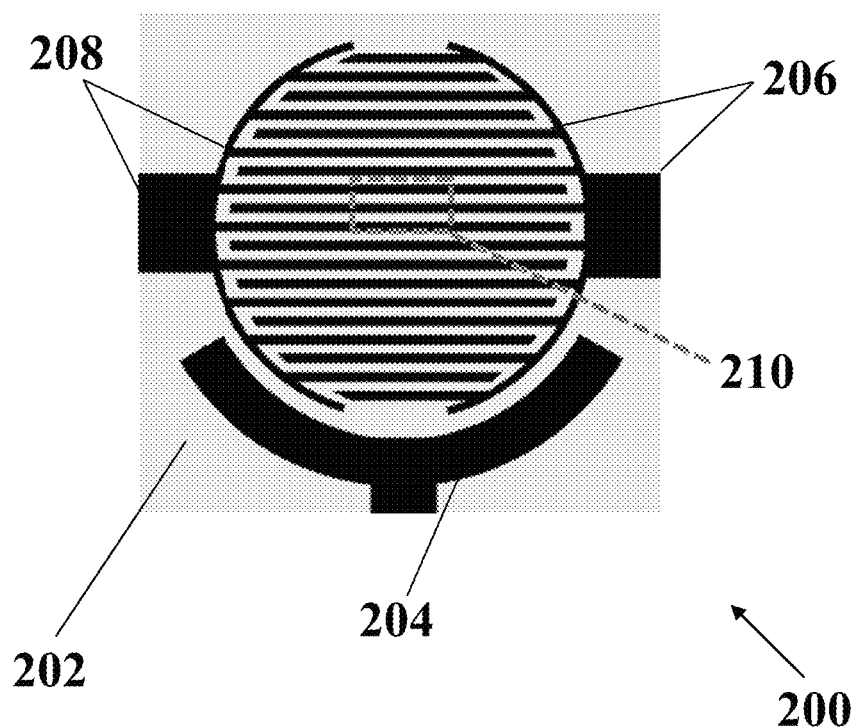
FIG. 2B illustrates a schematic top view of an exemplary electrochemical apparatus with an interdigital-patterned array of electrodes, consistent with one or more exemplary embodiments of the present disclosure.

FIG. 2B shows a schematic top view of an exemplary electrochemical apparatus 200 with an interdigital-patterned array of electrodes, consistent with one or more exemplary embodiments of the present disclosure. Exemplary interdigital-patterned array of electrodes may include a comb-patterned array of electrodes. Exemplary interdigital-patterned array of electrodes may include reference electrode 204, working electrode 206, and counter electrode 208, which may be patterned on exemplary substrate 202. Exemplary interdigital-patterned array of electrodes may include two arrays of teeth 206 and 208 which may be placed inside each other that may form working electrode 206 and counter electrode 208. Such interdigital or comb-shaped pattern of electrodes may lead to a uniform and dense distribution of the plurality of microbubbles generated through method 100 using exemplary electrochemical apparatus 200 with an interdigital-patterned array of electrodes.

Figure 2C:
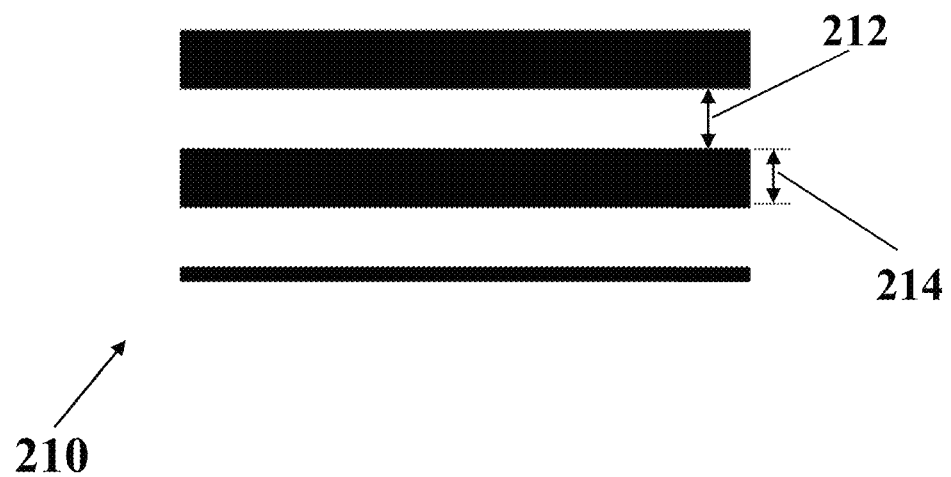
FIG. 2C shows a magnified schematic view of a portion of interdigital-patterned working electrode and counter electrode, consistent with one or more exemplary embodiments of the present disclosure.

FIG. 2C shows a magnified schematic view of a portion 210 of interdigital-patterned working electrode 206 and counter electrode 208, consistent with one or more exemplary embodiments of the present disclosure. In an exemplary embodiment, distance 212 between each two teeth of the working electrode 206 and counter electrode 208 may be in a range of between about 5 µm and about 200 µm. In an exemplary embodiment, a width 214 of each tooth of exemplary working electrode 206 or counter electrode 208 may be in a range of between about 5 µm and about 200 µm. In an exemplary embodiment, distance 212 between each two teeth of the working electrode 206 and counter electrode 208, and width 214 of each tooth of exemplary working electrode 206 or counter electrode 208 may have the same length, which may be in a range of between about 5 µm and about 200 µm. In an exemplary embodiment, the distance 212 between each two teeth of the working electrode 206 and counter electrode 208 may be in a range of between about 5 µm and about 50 µm. In an exemplary embodiment, a width 214 of each tooth of exemplary working electrode 206 or counter electrode 208 may be in a range of between about 5 µm and about 50 µm. In an exemplary embodiment, distance 212 between each two teeth of the working electrode 206 and counter electrode 208, and width 214 of each tooth of exemplary working electrode 206 or counter electrode 208 may have the same length, which may be in a range of between about 5 µm and about 50 µm.

Figure 1D:
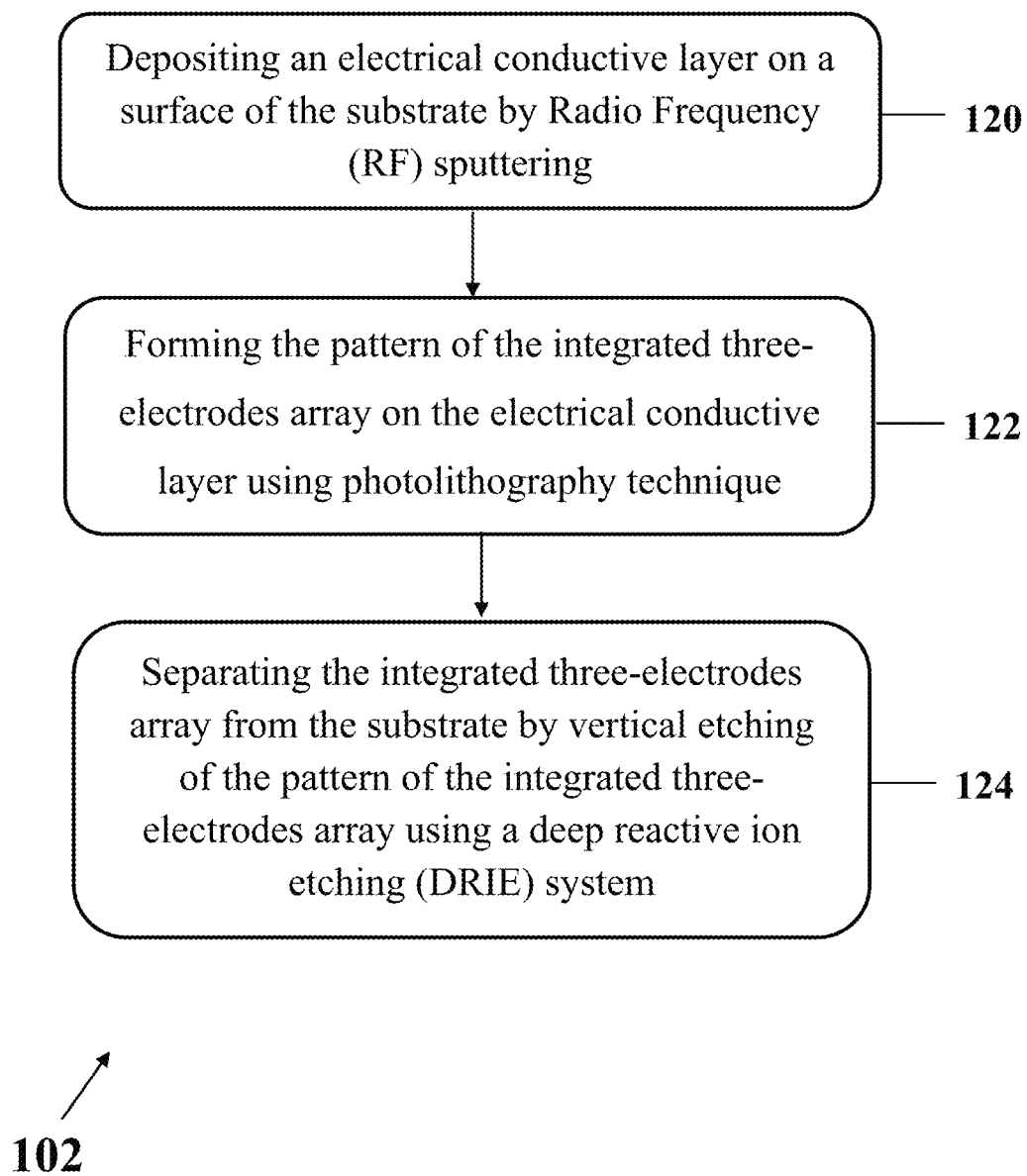
FIG. 1D illustrates an exemplary implementation of a process for preparing the electrochemical apparatus, consistent with one or more exemplary embodiments of the present disclosure.

In an exemplary implementation, preparing the electrochemical apparatus (step 102) may further include separating the integrated three-electrodes array from the substrate. FIG. 1D shows an exemplary implementation of a process for preparing exemplary electrochemical apparatus (step 102), consistent with one or more exemplary embodiments of the present disclosure. Preparing an exemplary electrochemical apparatus may include depositing the electrical conductive layer on the surface of the substrate by Radio Frequency (RF) sputtering (step 120), forming the pattern of the integrated three-electrodes array on the electrical conductive layer using photolithography technique (step 122), and separating the integrated three-electrodes array from the substrate (step 124). In an exemplary embodiment, separating the integrated three-electrodes array from the substrate may be carried out by vertical etching of the pattern of the integrated three-electrodes array using one of a reactive ion etching (RIE) system or a deep reactive ion etching (DRIE) system.

Figure 2D:
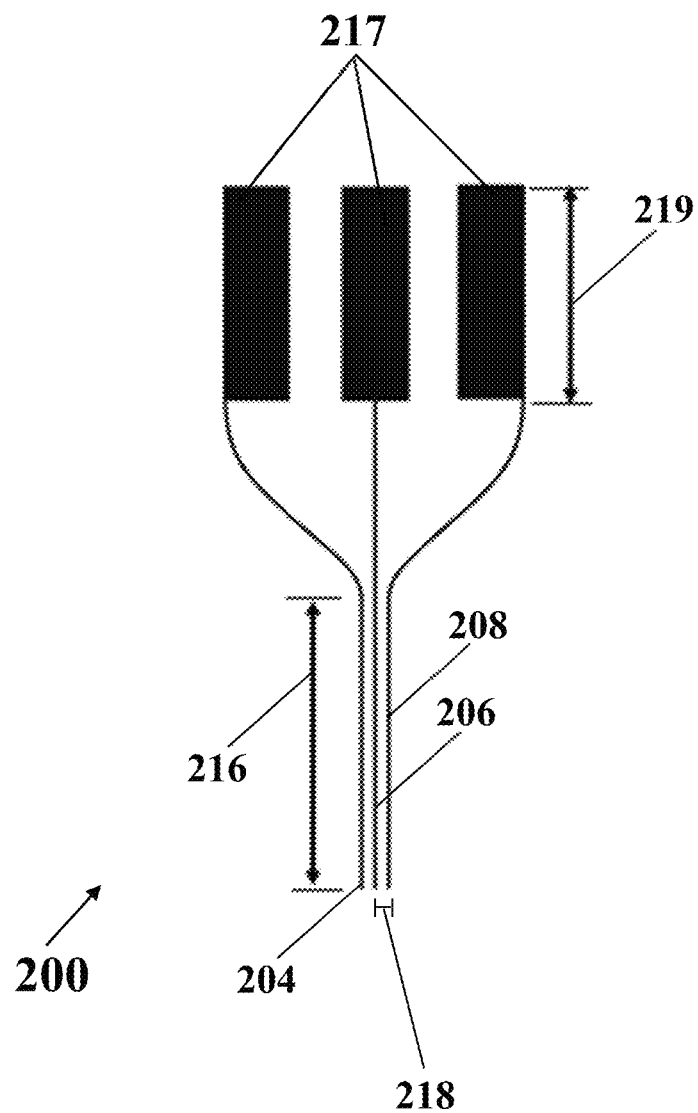
FIG. 2D illustrates a schematic side view of an exemplary electrochemical apparatus with needle-shaped array of electrodes, consistent with one or more exemplary embodiments of the present disclosure.
Figure 2E:
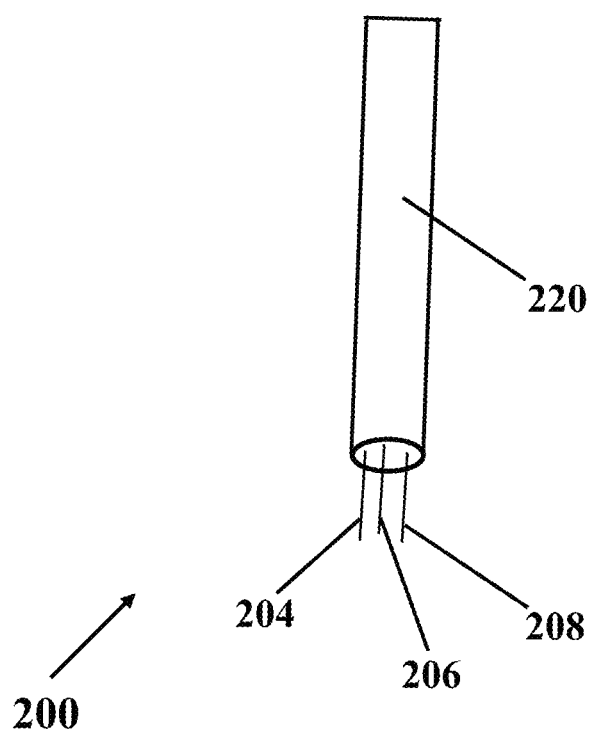
FIG. 2E illustrates a schematic view of an exemplary electrochemical apparatus with needle-shaped array of electrodes, consistent with one or more exemplary embodiments of the present disclosure.

In an exemplary implementation, exemplary electrochemical apparatus 200 may include an integrated three-electrodes array, where each electrode of the integrated three-electrodes array may include a needle. FIG. 2D shows a schematic side view of exemplary electrochemical apparatus 200 with needle-shaped array of electrodes, consistent with one or more exemplary embodiments of the present disclosure. Exemplary electrochemical apparatus 200 may include three needle-like electrodes that may include reference electrode 204, working electrode 206, and counter electrode 208. FIG. 2E shows a schematic view of exemplary electrochemical apparatus 200 with needle-shaped array of electrodes, consistent with one or more exemplary embodiments of the present disclosure. Referring to FIGS. 2D and 2E, each electrode of electrodes 204, 206, and 208 may include a respective needle 204, 206, and 208 that may include a needle with a length 216 in a range of about 5 mm to about 20 mm, for example, about 15 mm, and an exemplary distance 218 between each two needles may be in a range of about 50 µm to about 200 µm, for example, about 100 µm. In an exemplary embodiment, exemplary electrochemical apparatus 200 may include three electrical pads 217 with a length 219 of about 10 mm. Electrical pads 217 may connect three needle electrodes array 204, 206, and 208 to an electrochemical stimulator-analyzer system, for example, a potentiostat. In an exemplary embodiment, exemplary electrochemical apparatus 200 may include a fixed portion 220 that may hold needle-shaped array of electrodes. In an exemplary embodiment, thickness of each electrode of electrodes 204, 206, and 208 may be in a range of about 50 μm to about 200 μm, for example, about 100 μm.

In an exemplary implementation, exemplary process 102 for preparing exemplary electrochemical apparatus 200 with exemplary needle-shaped array of electrodes may include depositing a layer of a mechanically-resistant material on the substrate using RF sputtering (step 120), forming the pattern of the integrated three-electrodes array on the substrate with the layer of the mechanically-resistant material using photolithography technique (step 122), and separating the integrated three-electrodes array from the substrate with the layer of the mechanically-resistant material using one of a reactive ion etching (RIE) system or a deep reactive ion etching (DRIE) system (step 124). In an exemplary embodiment, the integrated three-electrodes array may be separated from the substrate with the layer of the mechanically-resistant material by vertical etching of the pattern of the integrated three-electrodes array in a deep reactive ion etching (DRIE) equipment. In an exemplary embodiment, the substrate may include one of a glass slide, Poly(methyl methacrylate) (PMMA), a silicon wafer, and combinations thereof. In an exemplary embodiment, the layer of the mechanically-resistant material may include a layer of Chrome (Cr). In an exemplary embodiment, the layer of the mechanically-resistant material may have a thickness of about 200 nm or less. In an exemplary embodiment, the layer of the mechanically-resistant material may have a thickness of about 100 nm.

Step 104 may include growing the nano-structured layer on exemplary working electrode 206 of the integrated three-electrode array of exemplary electrochemical apparatus 200. In an exemplary embodiment, nano-structured layer may include an array of electrically conductive, semi-conductive nanowires, or nanotubes with high mobility. In an exemplary embodiment, the nano-structured layer may include a layer of one of carbon nanotubes (CNTs), ZnO, Silicon nanowires (SiNWs), Silicon nanograss, $TiO_2$ nanotubes, $TiO_2$ nanowires, and combinations thereof. In an exemplary embodiment, the nano-structured layer may act as an active array of electrodes. In an exemplary embodiment, exemplary working electrode 206 may include an exemplary nano-structured layer grown thereon.

Figure 1E:
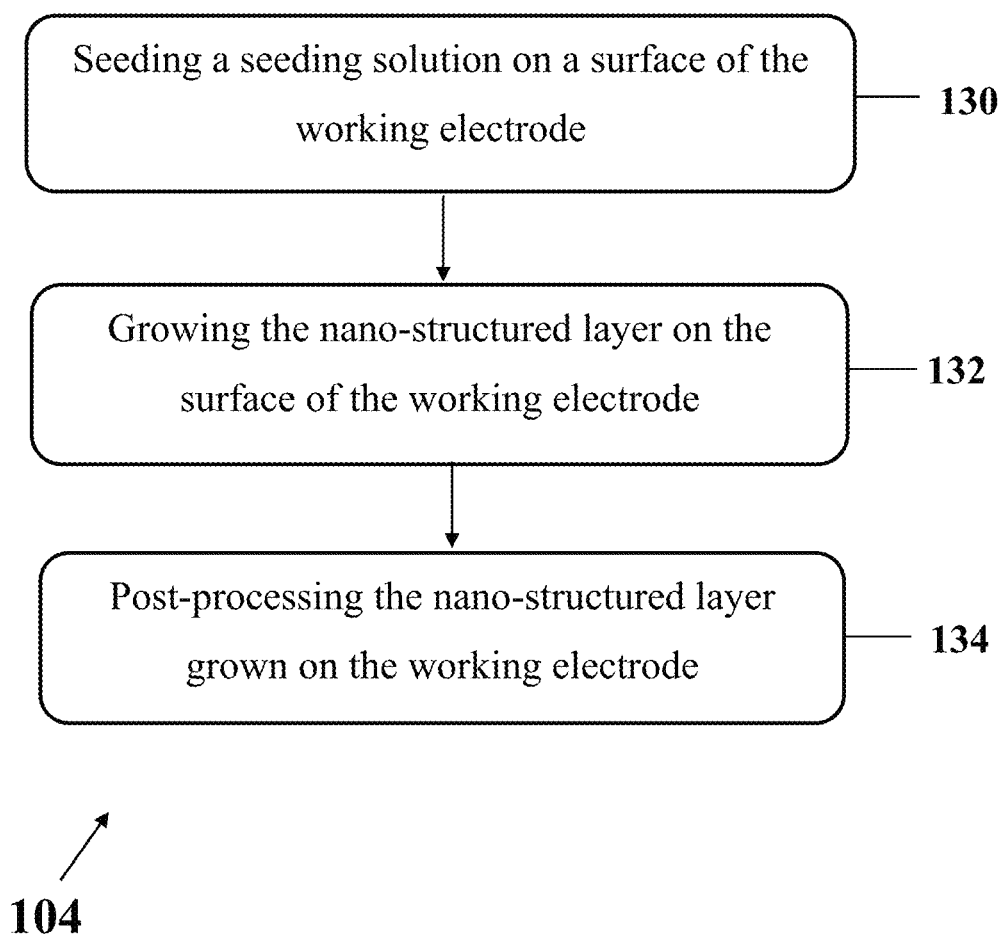
FIG. 1E shows an exemplary implementation of a process for growing the nano-structured layer on exemplary working electrode of the integrated three-electrodes array, consistent with one or more exemplary embodiments of the present disclosure.

FIG. 1E shows an exemplary implementation of a process for growing the nano-structured layer on exemplary working electrode 206 of the integrated three-electrodes array (step 104), consistent with one or more exemplary embodiments of the present disclosure. Exemplary process may be utilized for growing a layer of nano-structured ZnO, for example, ZnO nanotubes or ZnO nanowires on exemplary working electrode 206 of the integrated three-electrodes array. In an exemplary implementation, growing the nano-structured layer on exemplary working electrode 206 of the integrated three-electrodes array (step 104) may include seeding a seeding solution on a surface of exemplary working electrode 206 (step 130), growing the nano-structured layer on the surface of exemplary working electrode 206 (step 132), and post-processing the nano-structured layer grown on exemplary working electrode 206 (step 134).

In an exemplary implementation, seeding the seeding solution on the surface of exemplary working electrode 206 (step 130) may include wetting the surface of the working electrode by the seeding solution, spin-coating the seeding solution on the surface of the working electrode, and annealing exemplary electrochemical apparatus 200. In an exemplary embodiment, annealing exemplary electrochemical apparatus 200 may include annealing or heating exemplary electrochemical apparatus 200 at a temperature of more than about 250° C. for a time duration between about 10 minutes and about 30 minutes.

In an exemplary implementation, growing the nano-structured layer on the surface of exemplary working electrode 206 (step 132) may include placing exemplary electrochemical apparatus 200 in a sealed container including a growth solution and heating the sealed container uniformly at a temperature between about 70° C. and about 100° C. Exemplary electrochemical apparatus 200 may be placed in the sealed container and the sealed container may be placed in a water bath to control the temperature and heat uniformity.

In an exemplary implementation, post-processing the nano-structured layer grown on exemplary working electrode 206 (step 134) may include annealing exemplary electrochemical apparatus 200 at a temperature of more than about 250° C. for about 30 minutes. In an exemplary embodiment, exemplary electrochemical apparatus 200 may be annealed at a temperature of about 350° C. for about 30 minutes. Annealing may be carried out as a fabrication process in order to expose exemplary electrochemical apparatus 200 to a desired temperature using a low temperature furnace (below about 500° C.) or a high temperature furnace (above about 500° C.).

Step 106 may include putting exemplary electrochemical apparatus 200 in contact with the medium fluid. In an exemplary implementation, putting exemplary electrochemical apparatus 200 in contact with the medium fluid may include one of inserting the integrated three-electrodes array into a human body, inserting the integrated three-electrodes array into a cancer tumor, putting the electrochemical apparatus inside a biological solution, inserting the electrochemical apparatus into a cell culture medium, and combinations thereof. In an exemplary embodiment, the medium fluid may include a cell culture medium including a plurality of biological cells, for example, a Roswell Park Memorial Institute (RPMI) medium or a Dulbecco's Modified Eagle's Medium (DMEM) including a plurality of biological cells. In an exemplary embodiment, the medium fluid may include a body fluid. In an exemplary embodiment, the medium fluid may include a blood sample such as a blood serum.

Figure 3:
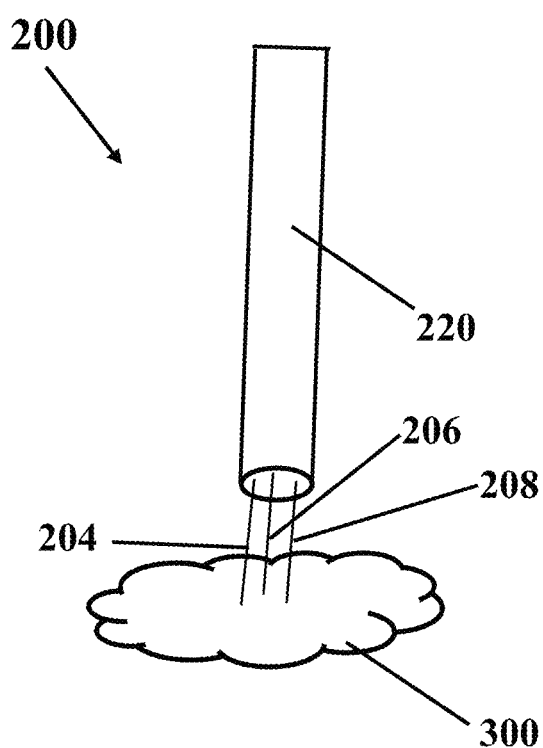
FIG. 3 illustrates a schematic implementation of putting exemplary electrochemical apparatus with needle-shaped array of electrodes in contact with an exemplary medium fluid, consistent with one or more exemplary embodiments of the present disclosure.

FIG. 3 shows a schematic implementation of putting exemplary electrochemical apparatus 200 with needle-shaped array of electrodes in contact with exemplary medium fluid 300, consistent with one or more exemplary embodiments of the present disclosure. In an exemplary embodiment, putting exemplary electrochemical apparatus 200 with needle-shaped array of electrodes in contact with exemplary medium fluid 300 may include squeezing or inserting exemplary needle-shaped array of exemplary electrochemical apparatus 200 with needle-shaped array of electrodes into a portion of a tissue of a human or animal body. In an exemplary embodiment, putting exemplary electrochemical apparatus 200 with needle-shaped array of electrodes in contact with exemplary medium fluid 300 may include squeezing or inserting exemplary needle-shaped array of exemplary electrochemical apparatus 200 with needle-shaped array of electrodes in a portion of a cancer tumor before a surgery, during a surgery, before or during a cancer treatment, or before or during a drug delivery procedure.

Step 108 may include electrolyzing exemplary medium fluid 300 by applying instantaneous electrical potential to the electrochemical apparatus in contact with exemplary medium fluid 300. In an exemplary implementation, electrolyzing exemplary medium fluid 300 by applying the instantaneous electrical potential to exemplary electrochemical apparatus 200 may include connecting exemplary electrochemical apparatus 200 to the electrochemical stimulator-analyzer system and applying the instantaneous electrical potential to exemplary working electrode 206 using the stimulator-analyzer system. In an exemplary implementation, electrolyzing exemplary medium fluid 300 by applying the instantaneous electrical potential to exemplary electrochemical apparatus 200 may include electrolyzing the medium fluid via a cyclic voltammetry (CV) technique.

Figure 4:
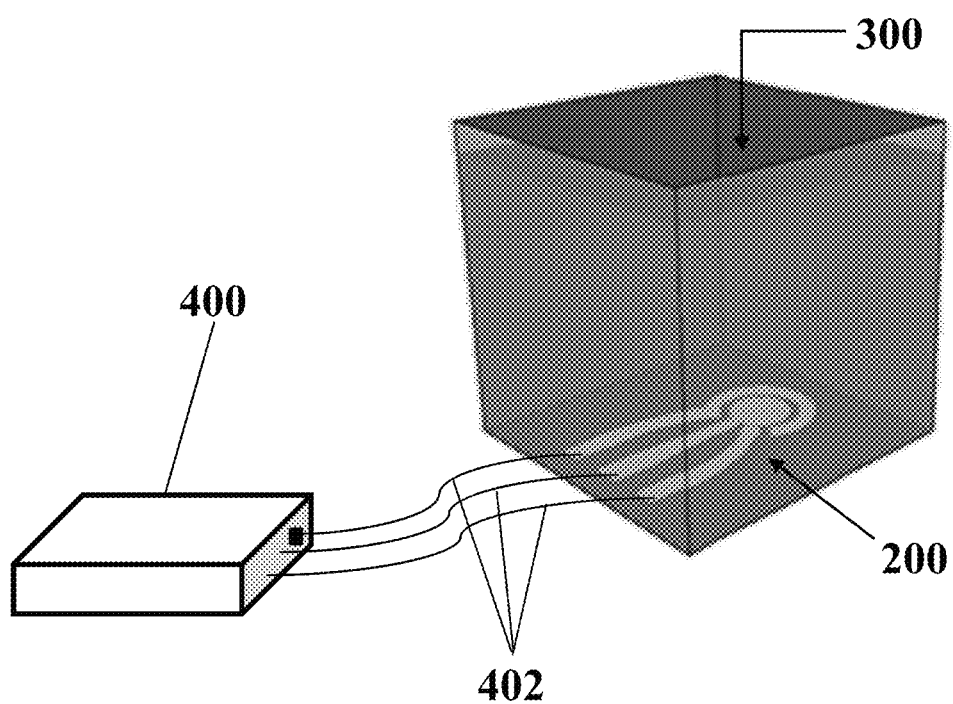
FIG. 4 illustrates a schematic exemplary implementation of exemplary electrochemical apparatus in contact with an exemplary medium fluid and connected to an exemplary electrochemical stimulator-analyzer system, consistent with one or more exemplary embodiments of the present disclosure.

FIG. 4 shows a schematic exemplary implementation of exemplary electrochemical apparatus 200 in contact with exemplary medium fluid 300 and connected to exemplary electrochemical stimulator-analyzer system 400, consistent with one or more exemplary embodiments of the present disclosure. In an exemplary embodiment, exemplary electrochemical stimulator-analyzer system 400 may include a potentiostat. In an exemplary embodiment, exemplary electrochemical apparatus 200 may be connected to exemplary electrochemical stimulator-analyzer system 400 via electrical connectors 402.

In an exemplary implementation, electrolyzing exemplary medium fluid 300 by applying an instantaneous electrical potential to exemplary electrochemical apparatus 200 may include applying a DC signal with a voltage between about −3 V and about −0.5 V for a time duration less than about 1 seconds to exemplary electrochemical apparatus 200 using exemplary stimulator-analyzer system 400. In an exemplary embodiment, electrolyzing exemplary medium fluid 300 by applying the instantaneous electrical potential to exemplary electrochemical apparatus 200 may include applying a DC signal with a voltage between about −2 V and about −0.1 V for a time duration less than about 1 seconds to exemplary electrochemical apparatus 200 using exemplary stimulator-analyzer system 400.

It should be noted that since a main portion of exemplary medium fluid 300 may include water in both in-vitro and in-vivo applications, the water may be electrolyzed near exemplary working electrode 206 during step 108. On the other hand, exemplary working electrode 206 may form a cathode electrode by applying the DC signal with a negative voltage between about −2 V and about −0.5 V. So the plurality of microbubbles generated around exemplary electrochemical apparatus 200 may include a plurality of $H_2$ microbubbles.

Step 110 may include generating the plurality of microbubbles around exemplary electrochemical apparatus 200 in contact with exemplary medium fluid 300. In an exemplary embodiment, step 110 may include generating the plurality of microbubbles around exemplary working electrode 206. In an exemplary embodiment, the plurality of microbubbles may include a plurality of $H_2$ microbubbles generated by electrolyzing exemplary medium fluid 300.

In an exemplary embodiment, a layer of the plurality of microbubbles generated via exemplary method 100 may remain on a surface of exemplary electrochemical apparatus 200 without suspending within exemplary medium fluid 300. Hence, generated microbubbles may be available near exemplary electrochemical apparatus 200, which may be inserted into one of a target part of a patient's body, a biopsied or resected sample of a tumor, a plurality of biological cells, etc. Therefore, generated microbubbles may be available near cells which may be targeted for an ultrasonic biomedical application, treatment, or procedure assisted by generated microbubbles. In an exemplary embodiment, the plurality of microbubbles may include a plurality of microbubbles with a diameter of less than about 200 μm. In an exemplary embodiment, the plurality of microbubbles may include a plurality of microbubbles with a diameter of less than about 20 μm. In an exemplary embodiment, the presence of the nano-structured layer on exemplary working electrode 206 may lead to decrease of a size or diameter of the plurality of microbubbles as well as increase in the number of the plurality of microbubbles generated around exemplary working electrode 206.

In an exemplary implementation, exemplary electrochemical apparatus 200 may include three electrically conductive needles integrated on a substrate or separately used. In an exemplary embodiment, exemplary electrochemical apparatus 200 may include three needles that may be put in contact with exemplary medium fluid 300 and on the other hand, the three needles may be connected to exemplary stimulator-analyzer system 400 to electrolyze exemplary medium fluid 300; thereby, resulting in generation of the plurality of microbubbles.

In an exemplary implementation, exemplary method 100 may be utilized for generating microbubbles within a biological cell media for ultrasonically-assisted biomedical applications using the biological cell media (the medium fluid) electrolysis. Exemplary method 100 may be utilized for generation of required microbubbles for efficiency enhancement of ultrasonically-assisted biomedical applications, such as targeted and increased drug delivery to cells, cells' sonoporation, etc. Using different patterns for integrated three-electrodes array, such as circular-patterned array (FIG. 2A), interdigital-patterned array (FIG. 2B), and needle-shaped array (FIG. 2D) may provide suitable implementations of exemplary electrochemical apparatus 200 for both in-vitro and in-vivo applications as well as suitable patterns of generated plurality of microbubbles depending on the application and conditions.

EXAMPLE 1

Generation of Microbubbles on Exemplary Electrochemical Apparatus with the Circular-Patterned Array of Electrodes In this example, an exemplary electrochemical apparatus 200 with a circular-patterned array was fabricated through exemplary step 102 described hereinabove. To fabricate exemplary electrochemical apparatus, Poly(methyl methacrylate) (PMMA/Plexiglass®) was used as the substrate.

Figure 5:
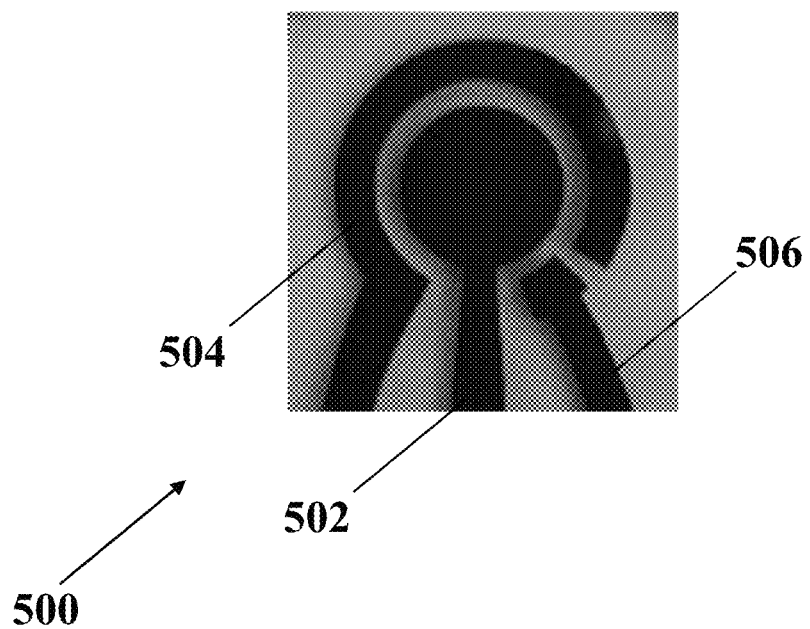
FIG. 5 illustrates an optical image of exemplary electrochemical apparatus with three-integrated circular-patterned electrodes as an exemplary electrochemical apparatus with a circular-patterned array, consistent with one or more exemplary embodiments of the present disclosure.

FIG. 5 shows an optical image of exemplary electrochemical apparatus 500 with three-integrated circular-patterned electrodes as an exemplary electrochemical apparatus 200 with a circular-patterned array, consistent with one or more exemplary embodiments of the present disclosure. Exemplary fabricated electrochemical apparatus 500 includes a circular working electrode 502 with a diameter of about 5 mm surrounded by a ring shaped counter electrode 504 with a thickness of about 1 mm and a reference electrode 506. The distance between counter electrode 504, reference electrode 506, and working electrode 502 is about 1 mm.

Exemplary electrochemical apparatus 500 was put within a cell culture media and connected to a potentiostat device. An instantaneous voltage of about −1.7 V was applied to the electrochemical apparatus 500; thereby, resulting in electrolysis of the cell culture media so that a plurality of microbubbles were generated around the electrochemical apparatus 500. It was observed that using a circular-patterned array of electrodes, most of the microbubbles were formed on the edges of the exemplary working electrode 502 and counter electrode 504 due to the edge effect in a circular pattern.

EXAMPLE 2

Generation of Microbubbles on Exemplary Electrochemical Apparatus with the Interdigital-Patterned Array of Electrodes In this example, two examples of exemplary electrochemical apparatus 200 with an interdigital-patterned array of electrodes was fabricated through exemplary step 102 described hereinabove. An exemplary electrochemical apparatus 200 with a bare interdigital-patterned array of electrodes and an exemplary electrochemical apparatus 200 with an interdigital-patterned array of electrodes covered by a layer of ZnO nanotubes were fabricated. To fabricate exemplary electrochemical apparatus 200, Poly(methyl methacrylate) (PMMA/Plexiglass®) was used as the substrate.

The synthesis of ZnO nanowires on exemplary electrochemical apparatus 200 included three steps of seeding, growth, and post processing. Prior to synthesis, exemplary electrochemical apparatus 200 was rinsed using detergent, deionized water, and acetone. Then, exemplary electrochemical apparatus 200 was dried in purified air flow. During the seeding step, the favorable areas of exemplary electrochemical apparatus 200 (working electrode surface) was spin coated by a 10 mM solution of zinc acetate dihydrate ($Zn(CH_3COO)_2.2H_2O$) in acetone. Exemplary electrochemical apparatus 200 was wetted with the aforementioned solution and then spin-coated at 2000 rpm for about 20 seconds. To accomplish the seeding step, exemplary electrochemical apparatus 200 was annealed at about 350° C. for about 20 minutes. A growth solution containing about 180 ml of 25 mM zinc nitrate hexahydrate ($Zn(NO_3)_2.6H_2O$), about 12.5 mM hexamethylenetetramine (($CH_2$)$_6N_4$), about 5 mM polyethylenimine, about 0.8 M ammonium hydroxide ($NH_4OH$), and deionized water was prepared. Exemplary electrochemical apparatus 200 was placed in a sealed container of the growth solution and the container was placed in a water bath to control the temperature and the heat uniformity. Subsequently, the container was heated in a microwave oven at about 850 watts for about 60 minutes. Afterwards, Exemplary electrochemical apparatus 200 was cleaned with deionized water and was then annealed for about 30 minutes at 350° C.

Exemplary electrochemical apparatus with the interdigital-patterned array of electrodes was put within a cell culture media and connected to a potentiostat device. An instantaneous voltage of about −1.4 V was applied to the electrochemical apparatus in order to electrolyze the cell culture media, so a plurality of microbubbles were generated around the electrochemical apparatus.

Figure 6A:
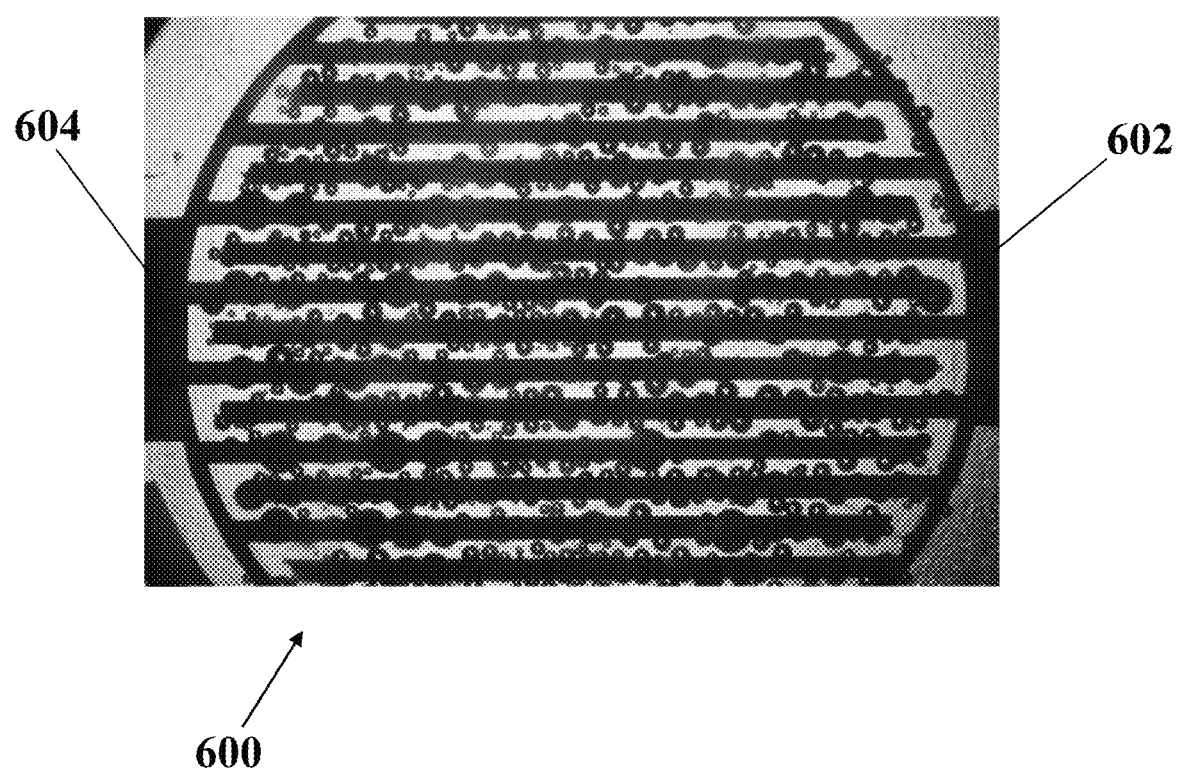
FIG. 6A illustrates an optical image of microbubbles generated on an exemplary electrochemical apparatus with bare interdigital-patterned electrodes, consistent with one or more exemplary embodiments of the present disclosure.
Figure 6B:
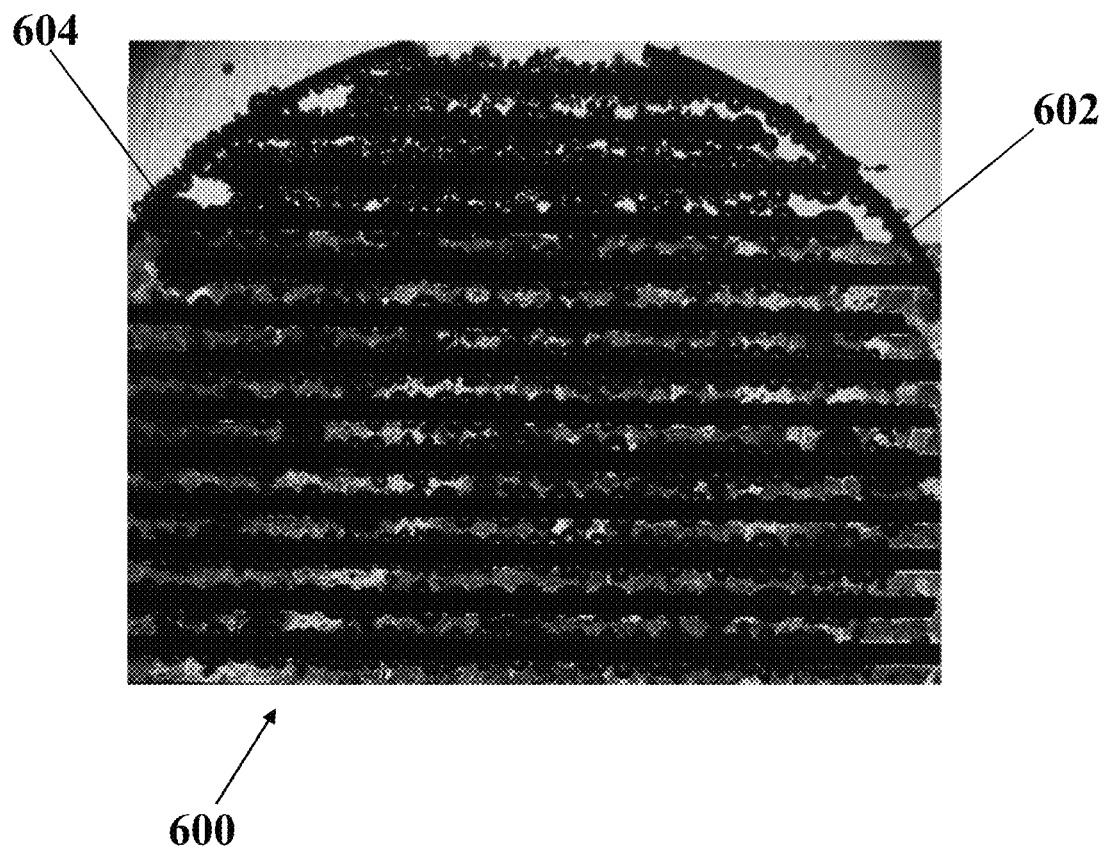
FIG. 6B illustrates an optical image of microbubbles generated on an exemplary electrochemical apparatus with interdigital-patterned electrodes coated by a layer of nano-structured ZnO, consistent with one or more exemplary embodiments of the present disclosure.

FIGS. 6A and 6B show optical images of exemplary microbubbles generated around exemplary working electrode 602 and counter electrode 604 of exemplary electrochemical apparatus 600 with interdigital-patterned electrodes, consistent with one or more exemplary embodiments of the present disclosure. In exemplary embodiments, electrochemical apparatus 600 may be similar to electrochemical apparatus 200, and electrodes 602 and 604 may be similar to working electrode 206 and counter electrode 208, respectively. FIG. 6A shows an optical image of microbubbles generated on exemplary electrochemical apparatus 600 with bare interdigital-patterned electrodes, consistent with one or more exemplary embodiments of the present disclosure. FIG. 6B shows an optical image of microbubbles generated on exemplary electrochemical apparatus 600 with interdigital-patterned electrodes coated by a layer of nano-structured ZnO, consistent with one or more exemplary embodiments of the present disclosure.

Referring to FIGS. 6A and 6B, it may be observed that using an interdigital-patterned array of electrodes, microbubbles are formed with uniformity all over the surface of exemplary electrochemical apparatus 600 on all teeth of exemplary working electrode 602 and counter electrode 604. The interdigital pattern in comparison with a circular pattern may benefit from the existence of edges all over the surface of exemplary electrochemical apparatus 600 which may cause a uniform production of microbubbles. By comparing FIG. 6A and FIG. 6B, it may be concluded that ZnO nanostructures cause an upward surge in the number of the produced microbubbles due to the abundance of the edges and number of microbubble generation sites as well as decreasing the size of microbubbles.

EXAMPLE 3

Generation of Microbubbles on Exemplary Electrochemical Apparatus with the Needle-Shaped Array of Electrodes In this example, two variations of exemplary electrochemical apparatus 200 with a needle-shaped array of electrodes were fabricated through exemplary step 102 described hereinabove. An exemplary electrochemical apparatus 200 with a bare needle-shaped array of electrodes and an exemplary electrochemical apparatus 200 with a needle-shaped array of electrodes covered by a layer of ZnO nanostructures were fabricated. To fabricate exemplary electrochemical apparatus, a layer of Chrome was deposited on a silicon wafer using RF sputtering. Then, three-electrode array was patterned on the Chrome deposited wafer by lithography process. Three-electrode pattern was removed by vertical etching in a deep reactive ion etching (DRIE) equipment. In case of fabrication of exemplary electrochemical apparatus 200 with a needle-shaped array of electrodes covered by a layer of ZnO nanostructures, ZnO nanostructures were grown on the needles.

The synthesis of ZnO nanostructures on exemplary electrochemical apparatus 200 included three steps of seeding, growth, and post processing. Prior to synthesis, exemplary electrochemical apparatus 200 was rinsed using detergent, deionized water, and acetone. Then, exemplary electrochemical apparatus 200 was dried in purified air flow. During the seeding step, the favorable areas of exemplary electrochemical apparatus 200 (working electrode surface) was spin coated by a 10 mM solution of zinc acetate dihydrate ($Zn(CH_3COO)_2.2H_2O$) in acetone. Exemplary electrochemical apparatus 200 was wetted with the aforementioned solution and then spin-coated at 2000 rpm for about 20 seconds. To accomplish the seeding step, exemplary electrochemical apparatus 200 was annealed at about 350° C. for about 20 min. A growth solution containing about 180 ml of 25 mM zinc nitrate hexahydrate ($Zn(NO_3)$ $_2$.6H$_2$O), about 12.5 mM hexamethylenetetramine ((CH¬$_2$)6N$_4$), about 5 mM polyethylenimine, about 0.8 M ammonium hydroxide (NH$_4$OH) and deionized water was prepared. Exemplary electrochemical apparatus 200 was drowned in a sealed container of the growth solution and the container was placed in a water bath to control the temperature and the heat uniformity. Subsequently, the container was heated in a microwave oven at about 850 watts for about 60 minutes. Afterwards, exemplary electrochemical apparatus 200 was cleaned with deionized water and was annealed for about 30 minutes at 350° C.

Figure 7A:
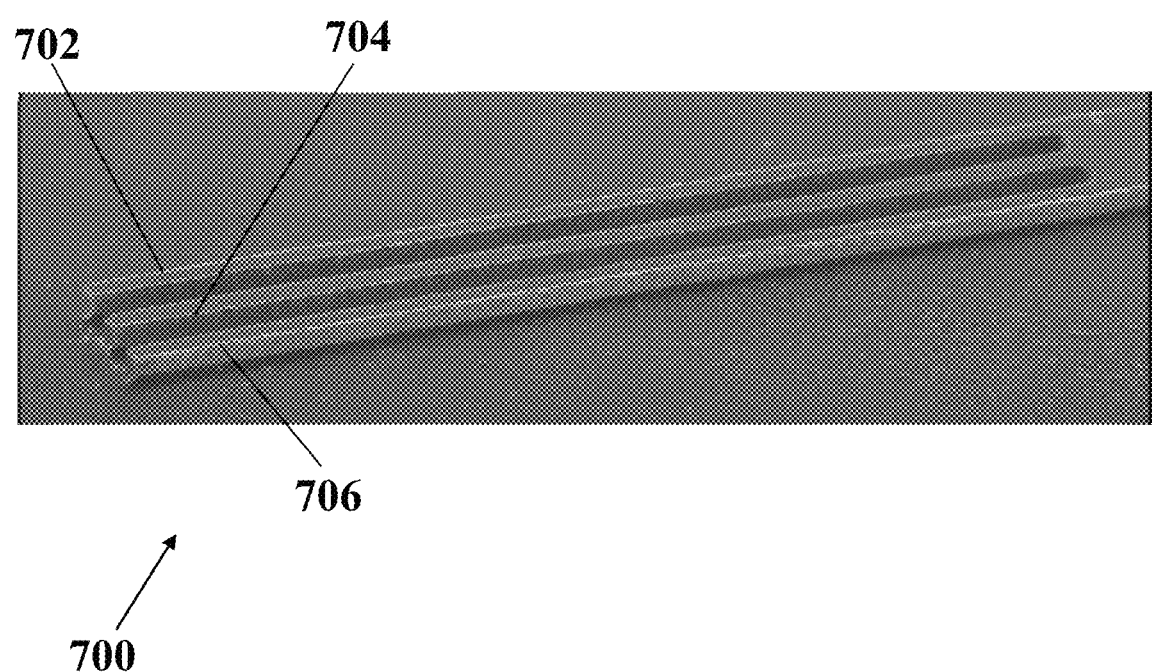
FIG. 7A illustrates a field emission scanning electron microscopy (FESEM) image of an exemplary electrochemical apparatus with three needle-shaped electrodes, consistent with one or more exemplary embodiments of the present disclosure.

FIG. 7A shows a field emission scanning electron microscopy (FESEM) image of exemplary electrochemical apparatus 700 with three needle-shaped electrodes including reference electrode 702, working electrode 704, and counter electrode 706, consistent with one or more exemplary embodiments of the present disclosure. In exemplary embodiments, electrochemical apparatus 700 may be similar to electrochemical apparatus 200, and reference electrode 702, working electrode 704, and counter electrode 706 may be similar to reference electrode 204, working electrode 206 and counter electrode 208, respectively.

Figure 7B:
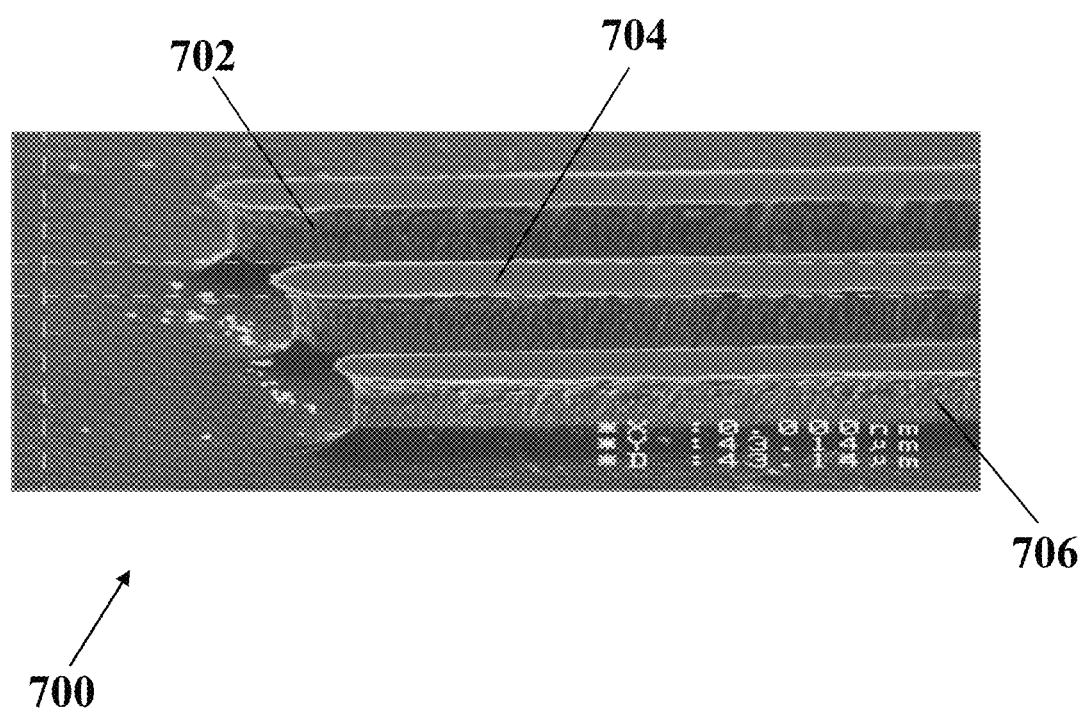
FIG. 7B illustrates a magnified FESEM image of an exemplary electrochemical apparatus with three needle-shaped electrodes, consistent with one or more exemplary embodiments of the present disclosure.

FIG. 7B shows a magnified FESEM image of exemplary electrochemical apparatus 700 with three needle-shaped electrodes, including reference electrode 702, working electrode 704, and counter electrode 706, consistent with one or more exemplary embodiments of the present disclosure. Each of the needles 702, 704, and 706 have a width of about 100 μm and are apart from each other with a distance of about 100 μm.

Figure 7C:
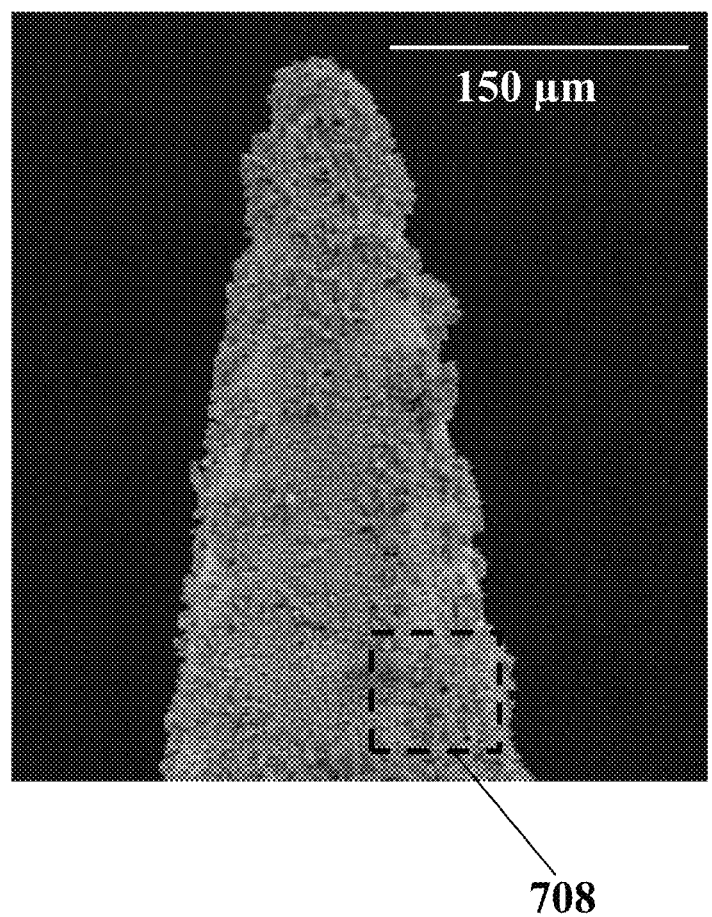
FIG. 7C illustrates a FESEM image of a tip of an exemplary working electrode coated with ZnO nanostructures, consistent with one or more exemplary embodiments of the present disclosure.
Figure 7D:
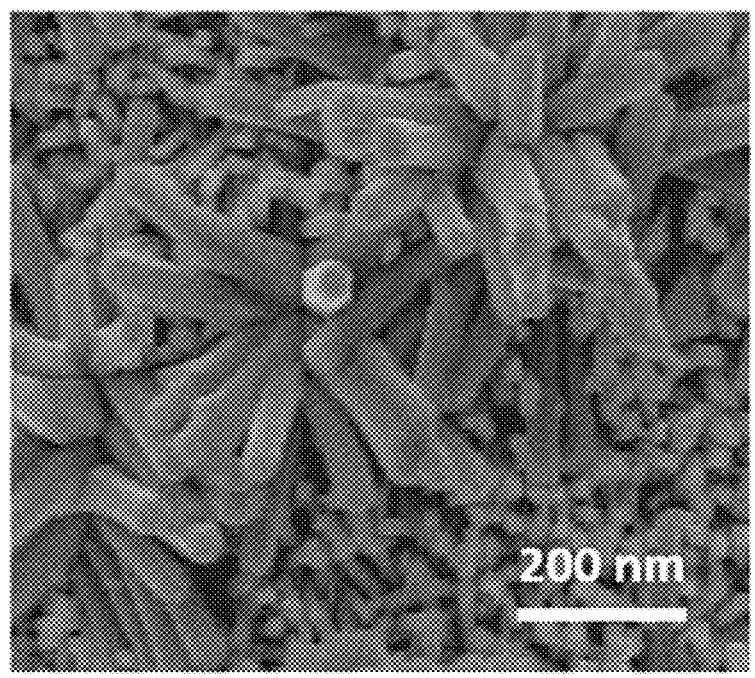
FIG. 7D illustrates a magnified FESEM image of a portion of the tip of an exemplary working electrode coated with ZnO nanostructures, consistent with one or more exemplary embodiments of the present disclosure.

FIG. 7C shows a FESEM image of a tip of exemplary working electrode 704 coated with ZnO nanostructures, consistent with one or more exemplary embodiments of the present disclosure. FIG. 7D shows a magnified FESEM image of a portion 708 (FIG. 7C) of the tip of exemplary working electrode 704 coated with ZnO nanostructures, consistent with one or more exemplary embodiments of the present disclosure.

Exemplary electrochemical apparatus with the interdigital-patterned array of electrodes was put in contact with a cell culture media and connected to a potentiostat device. An instantaneous voltage of about −2 V was applied to the electrochemical apparatus and a plurality of microbubbles were generated around the working electrode needle 704.

Figure 7E:
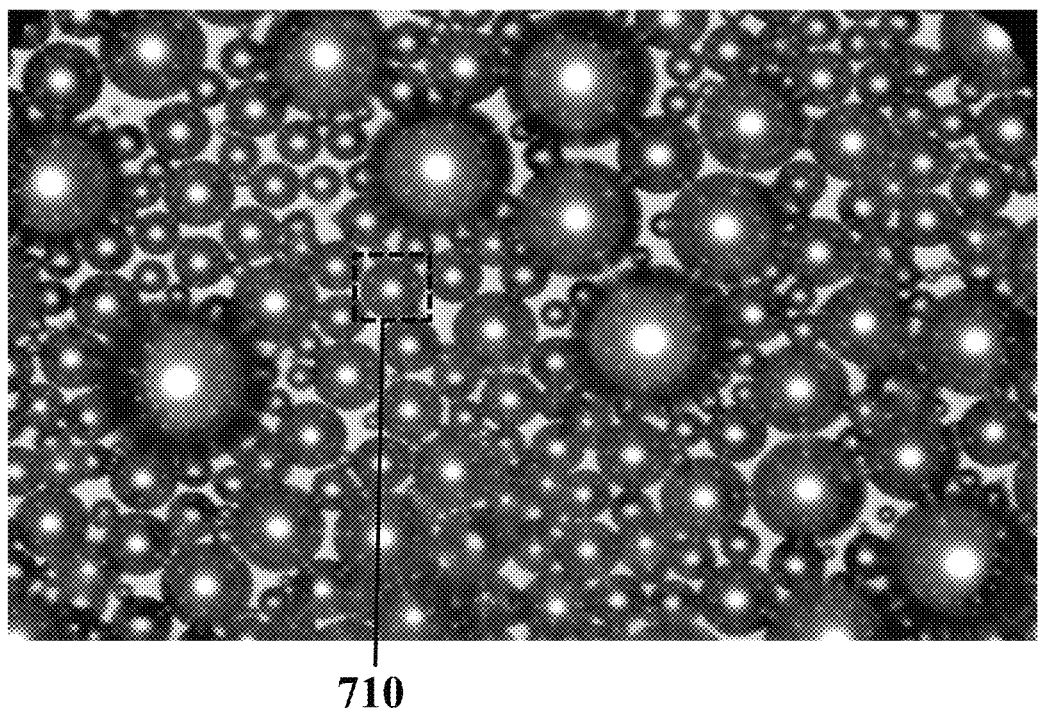
FIG. 7E illustrates an optical image of microbubbles generated on an exemplary electrochemical apparatus with bare needle electrodes, consistent with one or more exemplary embodiments of the present disclosure.
Figure 7F:
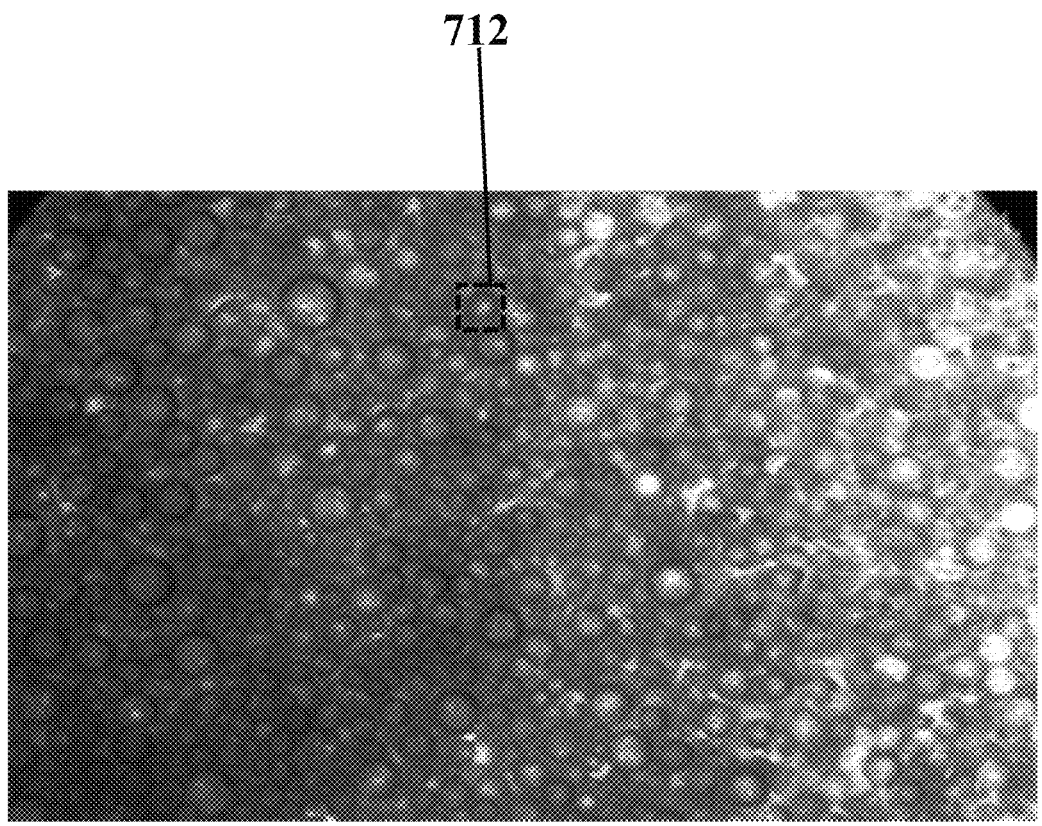
FIG. 7F illustrates an optical image of microbubbles generated on an exemplary electrochemical apparatus with needle-shaped electrodes coated by a layer of nano-structured ZnO, consistent with one or more exemplary embodiments of the present disclosure.

FIGS. 7E and 7F show optical images of exemplary microbubbles generated around exemplary working electrode 704 of exemplary electrochemical apparatus 700 with three needle-shaped electrodes, consistent with one or more exemplary embodiments of the present disclosure. FIG. 7E shows an optical image of microbubbles generated on exemplary electrochemical apparatus 700 with bare needle electrodes, consistent with one or more exemplary embodiments of the present disclosure. Exemplary microbubble 710 generated on exemplary electrochemical apparatus 700 with bare needle electrodes may have a size or a diameter of about 40 μm. FIG. 7F shows an optical image of microbubbles generated on exemplary electrochemical apparatus 700 with needle-shaped electrodes coated by a layer of nano-structured ZnO, consistent with one or more exemplary embodiments of the present disclosure. Exemplary microbubble 712 generated on exemplary electrochemical apparatus 700 with bare needle electrodes may have a size (a thickness or a diameter) of about 10 μm. It may be observed that ZnO nanostructures cause an upward surge in the number of the produced microbubbles as well as decreasing the size of microbubbles.

Figure 8A:
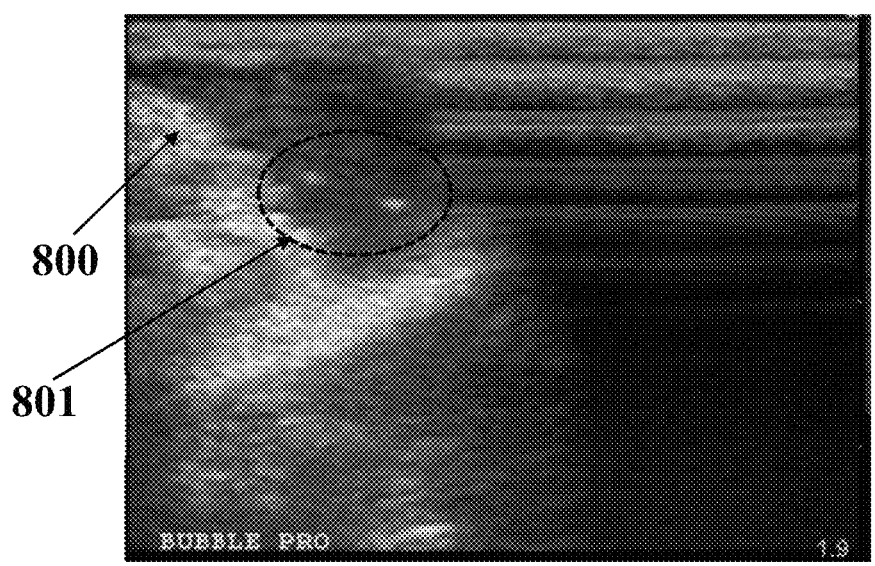
FIG. 8A illustrates a sonography image of a mouse tissue including microbubbles generated around an exemplary bare needle, consistent with one or more exemplary embodiments of the present disclosure.
Figure 8B:
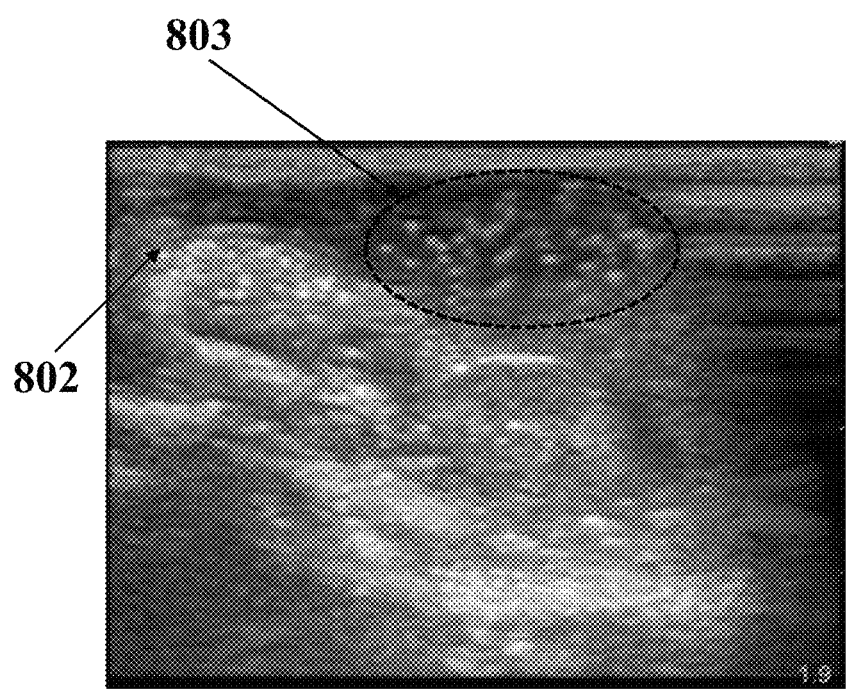
FIG. 8B illustrates a sonography image of a mouse tissue including microbubbles generated around an exemplary needle coated with a layer of ZnO nanostructures, consistent with one or more exemplary embodiments of the present disclosure.

In addition, sonography images were taken from mice tissue using exemplary electrochemical apparatus 700 with bare three needle-shaped electrodes and with three needle-shaped electrodes coated with a layer of ZnO nanostructures. FIG. 8A shows a sonography image of a mouse tissue including microbubbles generated around exemplary bare needle 800, consistent with one or more exemplary embodiments of the present disclosure. FIG. 8B shows a sonography image of a mouse tissue including microbubbles generated around exemplary needle 802 coated with a layer of ZnO nanostructures, consistent with one or more exemplary embodiments of the present disclosure. A huge increase in the number of the produced microbubbles in mice tissue using nanostructured ZnO-coated needle compared to bare needle may be observed in sonography images. As it can be seen, microbubbles 801, generated using exemplary bare needle 800, include a relatively fewer number of microbubbles, whereas microbubbles 803 generated using exemplary needle 802 coated with a layer of ZnO nanostructures include a larger number of homogenously dispersed microbubbles 803 around exemplary needle 802 coated with a layer of ZnO nanostructures.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A method for in-situ generation of microbubbles, comprising:
    preparing an electrochemical apparatus, the electrochemical apparatus comprising an integrated three-electrode array patterned on a substrate, the integrated three-electrode array comprising:
        a working electrode;
        a reference electrode; and
        a counter electrode;
    growing a nano-structured layer on the working electrode of the integrated three-electrode array;
    putting the electrochemical apparatus in contact with a medium fluid, the medium fluid comprising at least one of a cell culture medium and a biological solution medium;
    electrolyzing the medium fluid by applying an instantaneous electrical potential to the electrochemical apparatus in contact with the medium fluid; and
    generating a plurality of microbubbles around the electrochemical apparatus in contact with the medium fluid responsive to the electrolyzing of the medium fluid.

2. The method of claim 1, wherein the substrate comprises at least one of a glass slide, Poly(methyl methacrylate) (PMMA), a silicon wafer, and combinations thereof.

3. The method of claim 1, wherein the integrated three-electrode array comprises at least one of a circular-patterned array, an interdigital-patterned array, a needle-shaped array, and combinations thereof.

4. The method of claim 1, wherein preparing the electrochemical apparatus comprises:
    depositing an electrical conductive layer on a surface of the substrate by Radio Frequency (RF) sputtering; and
    forming a pattern of the integrated three-electrode array on the electrical conductive layer using photolithography technique.

5. The method of claim 4, wherein the electrical conductive layer comprises at least one of a mechanically-resistant material in reactive ion etching (RIE) system, a metal layer, a Gold/Titanium (Au/Ti) bilayer, a layer of Chrome (Cr), a layer of Gold (Au), and combinations thereof.

6. The method of claim 4, wherein preparing the electrochemical apparatus comprises:
    depositing a Gold/Titanium (Au/Ti) bilayer on the substrate, comprising:
        depositing a Ti layer on the substrate using a Radio Frequency (RF) sputtering system; and
        depositing an Au layer on the Ti layer using the Radio Frequency (RF) sputtering system; and
    patterning the integrated three-electrode array on the Au/Ti bilayer using photolithography technique.

7. The method of claim 4, wherein preparing the electrochemical apparatus further comprises treating the substrate by forming a non-conductive substrate from the substrate before depositing the electrical conductive layer on the surface of the substrate by Radio Frequency (RF) sputtering.

8. The method of claim 4, wherein preparing the electrochemical apparatus further comprises:
    separating the integrated three-electrode array from the substrate by vertical etching of the pattern of the integrated three-electrode array using a reactive ion etching (RIE) system.

9. The method of claim 1, wherein the nano-structured layer comprises a layer of at least one of carbon nanotubes (CNTs), ZnO, Silicon nanowires (SiNWs), Silicon nanograss, $TiO_2$ nanotubes, $TiO_2$ nanowires, and combinations thereof.

10. The method of claim 1, wherein growing the nano-structured layer on the working electrode of the integrated three-electrode array comprises:
    seeding a seeding solution on a surface of the working electrode, comprising:
        wetting the surface of the working electrode by the seeding solution;
        spin-coating the seeding solution on the surface of the working electrode; and
        annealing the electrochemical apparatus at a temperature of more than 250° C. for a time duration between 10 seconds and 30 seconds;
    growing the nano-structured layer on the surface of the working electrode, comprising:
        placing the electrochemical apparatus in a sealed container comprising a growth solution; and
        heating the sealed container uniformly at a temperature between 70° C. and 100° C.; and
    post-processing the nano-structured layer grown on the working electrode comprising annealing the electrochemical apparatus at a temperature of more than 250° C. for 30 minutes.

11. The method of claim 1, wherein putting the electrochemical apparatus in contact with the medium fluid comprises one of inserting the integrated three-electrode array into a human body, inserting the integrated three-electrode array into a cancer tumor, putting the electrochemical apparatus inside a biological solution, inserting the electrochemical apparatus into a cell culture medium.

12. The method of claim 1, wherein the medium fluid comprises a body fluid.

13. The method of claim 12, wherein the medium fluid comprises a blood sample.

14. The method of claim 1, wherein electrolyzing the medium fluid by applying the instantaneous electrical potential to the electrochemical apparatus comprises:
    connecting the electrochemical apparatus in contact with the medium fluid to an electrochemical stimulator-analyzer system; and
    applying the instantaneous electrical potential to the working electrode using the stimulator-analyzer system.

15. The method of claim 14, wherein the electrochemical stimulator-analyzer system comprises a potentiostat.

16. The method of claim 14, wherein electrolyzing the medium fluid by applying the instantaneous electrical potential to the electrochemical apparatus comprises applying a DC signal with a voltage between −3 V and −0.5 V for a time duration less than 1 seconds to the electrochemical apparatus using the stimulator-analyzer system.

17. The method of claim 1, wherein electrolyzing the medium fluid by applying the instantaneous electrical potential to the electrochemical apparatus comprises electrolyzing the medium fluid using a cyclic voltammetry (CV) technique.

18. The method of claim 1, wherein generating the plurality of microbubbles around the electrochemical apparatus in the medium fluid responsive to the electrolyzing the medium fluid comprises generating a plurality of microbubbles around the working electrode.

19. The method of claim 1, wherein the plurality of microbubbles comprises a plurality of $H_2$ microbubbles generated by electrolyzing the medium fluid.

* * * * *